US012767697B2

(12) United States Patent
Zhao et al.

(10) Patent No.: US 12,767,697 B2
(45) Date of Patent: Oct. 20, 2026

(54) GIP AND GLP-1 DUAL AGONIST POLYPEPTIDE COMPOUND, PHARMACEUTICALLY ACCEPTABLE SALT AND APPLICATION THEREOF

(71) Applicants: Sinopep-Allsino Biopharmaceutical Co., Ltd., Lianyungang (CN); Hangzhou Sinopep-Allsino Pharmaceutical Technology Development Co., Ltd., Hangzhou (CN)

(72) Inventors: Chengqing Zhao, Lianyungang (CN); Haitao Gu, Lianyungang (CN); Guoqiang Shi, Lianyungang (CN); Jianjun Jiang, Lianyungang (CN); Caidian Wang, Lianyungang (CN)

(73) Assignees: Sinopep-Allsino Biopharmaceutical Co., Ltd., Lianyungang (CN); Hangzhou Sinopep-Allsino Pharmaceutical Technology Development, Hangzhou (CN)

( * ) Notice: Subject to any disclaimer, the term of this patent is extended or adjusted under 35 U.S.C. 154(b) by 1231 days.

(21) Appl. No.: 17/717,034

(22) Filed: Apr. 8, 2022

(65) Prior Publication Data

US 2022/0251163 A1 Aug. 11, 2022

Related U.S. Application Data

(63) Continuation-in-part of application No. PCT/CN2019/110848, filed on Oct. 12, 2019.

(30) Foreign Application Priority Data

Oct. 8, 2019 (CN) ........................ 201910952193.3

(51) Int. Cl.

| | |
|---|---|
| ***C07K 14/605*** | (2006.01) |
| ***A61K 38/16*** | (2006.01) |
| ***A61K 45/06*** | (2006.01) |
| ***A61P 3/04*** | (2006.01) |
| ***A61P 3/10*** | (2006.01) |
| ***C07K 14/00*** | (2006.01) |

(52) U.S. Cl.

CPC ............ *C07K 14/605* (2013.01); *A61K 38/16* (2013.01); *A61K 45/06* (2013.01); *A61P 3/04* (2018.01); *A61P 3/10* (2018.01); *C07K 14/001* (2013.01)

(58) Field of Classification Search

CPC ....... C07K 14/605; C07K 14/72; A61K 38/16

See application file for complete search history.

(56) References Cited

U.S. PATENT DOCUMENTS

2014/0287994 A1* 9/2014 Bielicki ............... C07K 14/775 530/324

FOREIGN PATENT DOCUMENTS

| | | |
|---|---|---|
| CN | 107207576 A | 9/2017 |
| CN | 108135981 A | 6/2018 |
| CN | 108348583 A | 7/2018 |
| WO | 2011119657 A1 | 9/2011 |

OTHER PUBLICATIONS

Rao et al., Bull. Chem. Soc. Jpn., 70:293-299 (1997).*

P. F. Juan et al., The Sustained Effects of a Dual GIP/GLP-1 Receptor Agonist, NNC0090-2746, in Patients with Type 2 Diabetes, Cell Metabolism, Aug. 1, 2017, pp. 343-352, vol. 26, Cell Press, United States.

T. Coskun et al., LY3298176, a novel dual GIP and GLP-1 receptor agonist for the treatment of type 2 diabetes mellitus: From discovery to clinical proof of concept, Molecular Metabolism, Oct. 3, 2018, pp. 3-14, vol. 18, Elsevier GmbH, Germany.

P. F. Juan et al., Efficacy and safety of LY3298176, a novel dual GIP and GLP-1 receptor agonist, in patients with type 2 diabetes: a randomised, placebo-controlled and active comparator-controlled phase 2 trial, The Lancet, Oct. 4, 2018, pp. 2180-2193, vol. 392, Elsevier, United Kingdom.

Ju Yang et al., Dual co-agonist CI-1206 antagonizes Aβ1-42-induced impairments in spatial learning and memory in mice, Chinese Journal of Applied Physiology, Dec. 31, 2016, pp. 567-570, vol. 32 No. 6, China Academic Journal Electronic Publishing House, China.

* cited by examiner

*Primary Examiner* — Gyan Chandra

(74) *Attorney, Agent, or Firm* — MATTHIAS SCHOLL P.C.; Matthias Scholl

(57) ABSTRACT

A GIP and GLP-1 dual agonist polypeptide compound, having an amino acid sequence as follows:

(SEQ ID NO: 1)
$YXaa^1EGTFTSDYSIXaa^2LDKIAQXaa^3AFVQWLIAGGPSSGAPPPS$, and a C-terminal amino acid of polypeptide compound being amidated as a C-terminal primary amide.

1 Claim, 3 Drawing Sheets

Specification includes a Sequence Listing.

GIP AND GLP-1 DUAL AGONIST POLYPEPTIDE COMPOUND, PHARMACEUTICALLY ACCEPTABLE SALT AND APPLICATION THEREOF

CROSS-REFERENCE TO RELATED APPLICATIONS

This application is a continuation-in-part of International Patent Application No. PCT/CN2019/110848 with an international filing date of Oct. 12, 2019, designating the United States, now pending, and further claims foreign priority benefits to Chinese Patent Application No. 201910952193.3 filed Oct. 8, 2019. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to the field of polypeptide compounds, and more particularly to a double-intestinal insulinotropic peptide analogue, that is, a polypeptide compound. The polypeptide compound can activate receptors of human glucose-dependent insulinotropic polypeptide (GIP) and glucagon-like peptide-1 (GLP-1) and can be used for treating type 2 diabetes. The disclosure further relates to a pharmaceutically acceptable salt of the polypeptide compound, a polypeptide pharmaceutical composition, a method and an application thereof.

The pathogenesis of metabolic syndrome is abnormal metabolism of various substances such as protein, fat and carbohydrate. Overnutrition and reduced physical activity can lead to obesity and obesity-related diseases such as diabetes. In recent years, the incidence of type 2 diabetes and dyslipidemia is on the rise. Type 2 diabetes is characterized by high blood glucose levels caused by insulin resistance. The current standard of care for type 2 diabetes includes diet and exercise and the availability of oral and injectable hypoglycemic agents.

Glucose-dependent inotropic peptide (GIP) is a 42-amino acid gastrointestinal regulatory peptide that stimulates insulin secretion from pancreatic β-cells and protects pancreatic β-cells in the presence of glucose, playing a physiological role in glucose homeostasis. GLP-1 is a 37-amino acid peptide that stimulates insulin secretion, protects pancreatic β-cells, and inhibits glucagon secretion, gastric emptying, and food intake, resulting in weight loss. GIP and GLP-1 are known as incretin; Incretin receptor signaling transmission has a physiologically relevant role to maintain glucose homeostasis. In normal physiology, GIP and GLP-1 are secreted from the gut after a meal, and these incretins enhance physiological responses to foods, including satiety, insulin secretion, and nutrient processing. The incretin response is impaired in patients with type 2 diabetes. Currently commercially available incretin analogs or dipeptidyl peptidase IV (DPP-IV) inhibitors utilize a single mechanism of action for glycemic control; if a compound for type 2 diabetes with a dual mechanism of action is used, a polypeptide compound with excellent hypoglycemic activity and weight loss effect can be obtained.

It has been found that the dosage of GLP-1 analogs is limited by side effects such as nausea and vomiting, and therefore administration of a drug often cannot achieve the full efficacy in glycemic control and weight loss. GIP alone has very modest glucose-lowering capacity in patients with type 2 diabetes. Both native GIP and GLP-1 are rapidly inactivated by the ubiquitous protease DPP IV, therefore, they can only be used for short-term metabolic control. DPP IV belongs to the exopeptidase class of proteolytic enzymes; the introduction of unnatural amino acids into the sequence can increase the proteolytic stability of any given peptide, although unnatural amino acids help stabilize the peptide against DPP IV proteolysis and other forms of degradation.

SUMMARY

As a part of the disclosure, the unnatural amino acids positively affect the balance of agonist activity between GIP and GLP-1. For example, fatty acids can improve the pharmacokinetics of peptides by extending half-life through their albumin-binding motifs. While fatty acids can improve the half-life of peptides, the applicant has discovered that, as a part of the disclosure, the length, composition and location of the fatty acid chains and the linkers between the peptides and the fatty acid chains may have unexpected effect on the balance of activity of GIP and GLP-1 agonists while extending the half-life of the peptide.

One object of the disclosure is to provide a GIP and GLP-1 dual agonist polypeptide compound which exhibits blood glucose reducing activity and weight-losing effect.

Another object of the disclosure is to provide a method for preparing the GIP and GLP-1 dual agonist polypeptide compound.

Still another object of the disclosure is to provide a pharmaceutically acceptable salt of the GIP and GLP-1 dual agonist polypeptide compound.

Still another object of the disclosure is to provide a pharmaceutical composition of the GIP and GLP-1 dual agonist polypeptide compound.

Still another object of the disclosure is to provide a medicament of the GIP and GLP-1 dual agonist polypeptide compound.

Still another object of the disclosure is to provide the GIP and GLP-1 dual agonist polypeptide compound, a pharmaceutically acceptable salt thereof, a pharmaceutical composition thereof and an application of a medicament.

The disclosure provides a GIP and GLP-1 dual agonist polypeptide compound. The GIP and GLP-1 dual agonist polypeptide compound is characterized in that the amino acid sequence of the GIP and GLP-1 dual agonist polypeptide compound is $YXaa^1EGTFTSDYSIXaa^2LDKIAQXaa^3AFVQWLIAGGPSSGAPPPS$ (SEQ ID NO: 1), and the C-terminal amino acid of the polypeptide compound is amidated as C-terminal primary amide;

$Xaa^1$ is: V, Aib, A, 1-aminocyclobutane-1-carboxylic acid

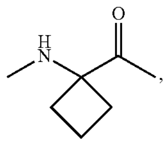
, 1-aminocyclopentane-1-carboxylic acid

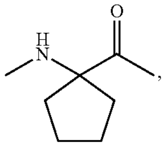
,
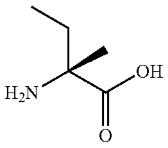

(R)-2-amino-2-methylbutanoic acid

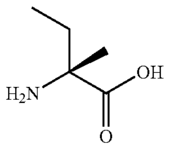

or (S)-2-amino-2-methylbutanoic acid

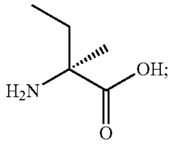

Xaa[2] is: V, Aib, A,

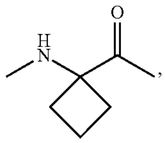
,
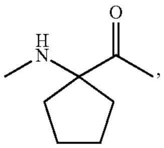
,
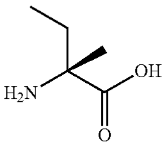
or
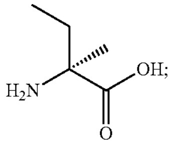

Xaa[1] and Xaa[2] are the same or different;
Xaa[3] is:

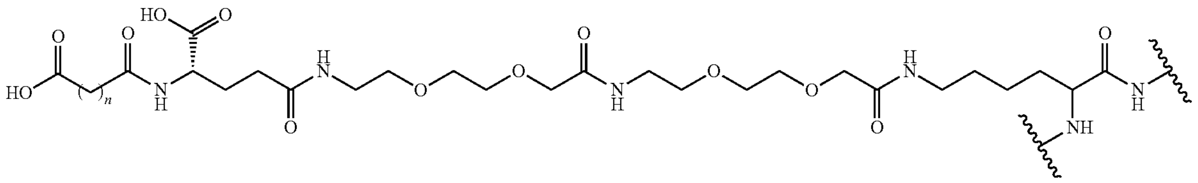

or:

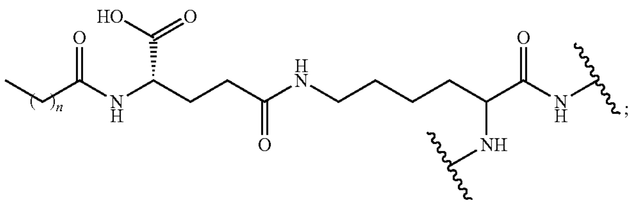

n is an integer number ranging from 5 to 25.

In a class of this embodiment, n is an integer number 16 or 18.

In a class of this embodiment, the amino acid sequence of the of polypeptide compound is preferably shown as follows:

(1) ID NO: 1
YVEGTFTSDYSIVLDKIAQK(HOOC-$(CH_2)_{16}$-CO-γ-Glu-AEEA-AEEA)AFVQWLIAGGPSSGAPPPS-$NH_2$ (2) ID NO: 2
YXEGTFTSDYSIXLDKIAQK(HOOC-$(CH_2)_{16}$-CO-γ-Glu-AEEA-AEEA)AFVQWLIAGGPSSGAPPPS-$NH_2$ (3) ID NO: 3
Y$X_1$EGTFTSDYSI$X_1$LDKIAQK(HOOC-$(CH_2)_{16}$-CO-γ-Glu-AEEA-AEEA)AFVQWLIAGGPSSGAPPPS-$NH_2$ (4) ID NO: 4
YAEGTFTSDYSIALDKIAQ(HOOC-$(CH_2)_{16}$-CO-γ-Glu-AEEA-AEEA)AFVQWLIAGGPSSGAPPPS-$NH_2$ (5) ID NO: 5
YAEGTFTSDYSIAibLDKIAQK(HOOC-$(CH_2)_{16}$-CO-γ-Glu-AEEA-AEEA)AFVQWLIAGGPSSGAPPPS-$NH_2$ (6) ID NO: 6
YAibEGTFTSDYSIALDKIAQK(HOOC-$(CH_2)_{16}$-CO-γ-Glu-AEEA-AEEA)AFVQWLIAGGPSSGAPPPS-$NH_2$ (7) ID NO: 7
YXEGTFTSDYSI$X_2$LDKIAQK(HOOC-$(CH_2)_{16}$-CO-γ-Glu-AEEA-AEEA)AFVQWLIAGGPSSGAPPPS-$NH_2$ (8) ID NO: 8
YXEGTFTSDYSI$X_2$LDKIAQK(HOOC-$(CH_2)_{16}$-CO-γ-Glu-AEEA-AEEA)AFVQWLIAGGPSSGAPPPS-$NH_2$

-continued (9)

ID NO: 9

Y$X_1$EGTFTSDYSI$X_2$LDKIAQK(HOOC-$(CH_2)_{16}$-CO-γ-Glu-AEEA-AEEA)AFVQWLIAGGPSSGAPPPS-$NH_2$ (10)

ID NO: 10

Y$X_2$EGTFTSDYSI$X_1$LDKIAQK(HOOC-$(CH_2)_{16}$-CO-γ-Glu-AEEA-AEEA)AFVQWLIAGGPSSGAPPPS-$NH_2$ (11)

ID NO: 11

YAibEGTFTSDYSIAibLDKIAQK(γ-Glu-Palmitoyl)AFVQWLIAGGPSSGAPPPS-$NH_2$ (12)

ID NO: 12

YVEGTFTSDYSIVLDKIAQK(γ-Glu-Palmitoyl)AFVQWLIAGGPSSGAPPPS-$NH_2$ (13)

ID NO: 13

YXEGTFTSDYSIXLDKIAQK(γ-Glu-Palmitoyl)AFVQWLIAGGPSSGAPPPS-$NH_2$ (14)

ID NO: 14

Y$X_1$EGTFTSDYSI$X_1$LDKIAQK(γ-Glu-Palmitoyl)AFVQWLIAGPSSGAPPPS-$NH_2$ (15)

ID NO: 15

YAEGTFTSDYSIALDKIAQK(γ-Glu-Palmitoyl)AFVQWLIAGGPSSGAPPPS-$NH_2$ (16)

ID NO: 16

YAEGTFTSDYSIAibLDKIAQK(γ-Glu-Palmitoyl)AFVQWLIAGGPSSGAPPPS-$NH_2$ (17)

ID NO: 17

YAibEGTFTSDYSIALDKIAQK(γ-Glu-Palmitoyl)AFVQWLIAGGPSSGAPPPS-$NH_2$ (18)

ID NO: 18

YXEGTFTSDYSI$X_2$LDKIAQK(γ-Glu-Palmitoyl)AFVQWLIAGGPSSGAPPPS-$NH_2$ (19)

ID NO: 19

Y$X_2$EGTFTSDYSIXLDKIAQK(γ-Glu-Palmitoyl)AFVQWLIAGGPSSGAPPPS-$NH_2$ (20)

ID NO: 20

Y$X_1$EGTFTSDYSI$X_2$LDKIAQK(γ-Glu-Palmitoyl)AFVQWLIAGGPSSGAPPPS-$NH_2$ (21)

ID NO: 21

Y$X_2$EGTFTSDYSI$X_1$LDKIAQK(γ-Glu-Palmitoyl)AFVQWLIAGGPSSGAPPPS-$NH_2$ wherein:

X = 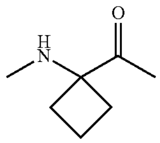 ; $X_1$= 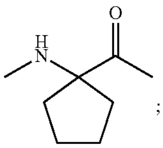 ;

$X_2$=Aib.

The disclosure also discloses a method for preparing the GIP and GLP-1 dual agonist polypeptide compound, the method comprising:

(1) taking a resin, activating the resin, and consecutively coupling amino acids to the resin to obtain a peptide resin; and (2) splicing a side chain to the peptide resin, splitting and purifying to obtain a side chain protected polypeptide.

The disclosure also discloses a pharmaceutically acceptable salt of the GIP and GLP-1 dual agonist polypeptide compound. The C-terminal amino acid of the polypeptide compound is amidated as C-terminal primary amide or the pharmaceutically acceptable salt is amidated.

For the pharmaceutically acceptable salt of the GIP and GLP-1 dual agonist polypeptide compound of the disclosure, optionally, the salt is a salt formed by GIP and GLP-1 dual agonist polypeptide compound and one of the following compounds: hydrochloric acid, hydrobromic acid, hydroiodic acid, sulfuric acid, pyrosulfuric acid, phosphoric acid; nitric acid, rnethanesulfonic acid, ethanesulfonic acid, benzenesulfonic acid; p-toluenesulfonic acid, formic acid; acetic acid, acetoacetic acid, pyruvic acid, trifluoroacetic acid, propionic acid, butyric acid, caproic acid, heptanoic acid; undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, niacin, pamoic acid, pectinic acid, persulfuric acid, 3-phenylpropionic acid, picric acid, pivalic acid, 2-hydroxyethanesulfonic acid, itaconic acid, sulfamic acid, trifluoromethanesulfonic acid, dodecyl sulfuric acid, 2-naphthalene sulfonic acid, naphthalenedisulfonic acid, camphor sulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, hemisulfuric acid or thiocyanic acid.

The disclosure also discloses a pharmaceutical composition comprising the GIP and GLP-1 dual agonist polypeptide compound. The pharmaceutical composition is prepared by taking the GIP and GLP-1 dual agonist polypeptide compound as an effective raw material or taking a pharmaceutically acceptable salt of any one GIP and GLP-1 dual agonist polypeptide compound in the technical solution as an effective raw material and mixing with a pharmaceutically acceptable carrier or diluent.

The pharmaceutically acceptable salt of the GIP and GLP-1 dual agonist polypeptide compound is prepared by taking the GIP and GLP-1 dual agonist polypeptide compound and the above compound as raw materials and adopting a conventional method disclosed in the prior art.

The disclosure also provides a medicament prepared from the GIP and GLP-1 dual agonist polypeptide compound. The medicament is in the form of a tablet, a capsule, an elixir, syrup, a lozenge, an inhalant, a spray, an injection, a film, a patch, powder, a granule, a block, an emulsion, a suppository or a compound preparation in pharmacy, and the medicament is prepared from the GIP and GLP-1 dual agonist polypeptide compound and a pharmaceutically acceptable pharmaceutic adjuvant, carrier or diluent. The medicament can be prepared according to a conventional method in the prior art.

According to the application of the GIP and GLP-1 dual agonist polypeptide compound in the disclosure, the GIP and GLP-1 dual agonist polypeptide compound can be used as an effective raw material for preparing a medicine for treating or preventing diabetes mellitus or preparing a weight-losing medicine.

According to the pharmaceutical application of the GIP and GLP-1 dual agonist polypeptide compound in the disclosure, the GIP and GLP-1 dual agonist polypeptide compound can be used as an effective raw material for preparing a medicine for treating or preventing diabetes mellitus or preparing a weight-losing medicine.

The pharmaceutical composition and the medicament of the GIP and GLP-1 dual agonist polypeptide compound in the disclosure can be used as an effective raw material for preparing a medicine for treating and preventing diabetes mellitus or a weight-losing medicine.

In this specification, the meanings of the following abbreviations are shown in the table below:

| Abbreviation | Meaning |
|---|---|
| DCM | Dichloro-methane |
| DMF | N-methylpyrrolidone |
| HBTU | Berizotriazole-N,N,N',N'-tetramethylurea hexafluorophosphate |
| HOBt | 1-hydroxy-benzotriazole |
| DIEA/DIPEA | N,N'-diisopropyleihylamine |
| Fmoc | N-9-fluorenemethoxycarbonyl |
| EDT | Ethanedithiol |
| HPLC | High performance liquid chromatography |
| TFA | Trifluoroacetate |
| tBu | Tert-butyl |
| DMSO | Dimethyl sulfoxide |
| Alloc | Allyloxycarbonyl |

The following advantages are associated with the GIP and GLP-1 dual agonist polypeptide compound:

The disclosure provides a novel GIP and GLP-1 dual agonist polypeptide compound. The polypeptide compound has the effects of reducing blood glucose and losing weight at the same time, and can be used as the effective raw material for preparing the medicine for treating or preventing diabetes or the weight-losing medicine. Based on animal energy consumption data, the polypeptide compound has the effect of losing weight of patients, has balanced co-agonist activity on GIP and GLP-1 receptors and selectivity on glucagon and GLP-2 receptors, has the characteristic of low irmmunogenicity and the pharmacokinetic (PK) characteristics supporting once-weekly dosing, and is suitable for serving as an active ingredient of a medicine for treating diabetes and obesity.

The GIP and GLP-1 dual agonist polypeptide compound prepared by the method has good activity of reducing blood glucose and slowing weight gain, and is long in effect time, high in yield, short in synthesis period, easy in crude product purification, low in production cost and easy for automatic industrial production.

DETAILED DESCRIPTION

Figure 1:
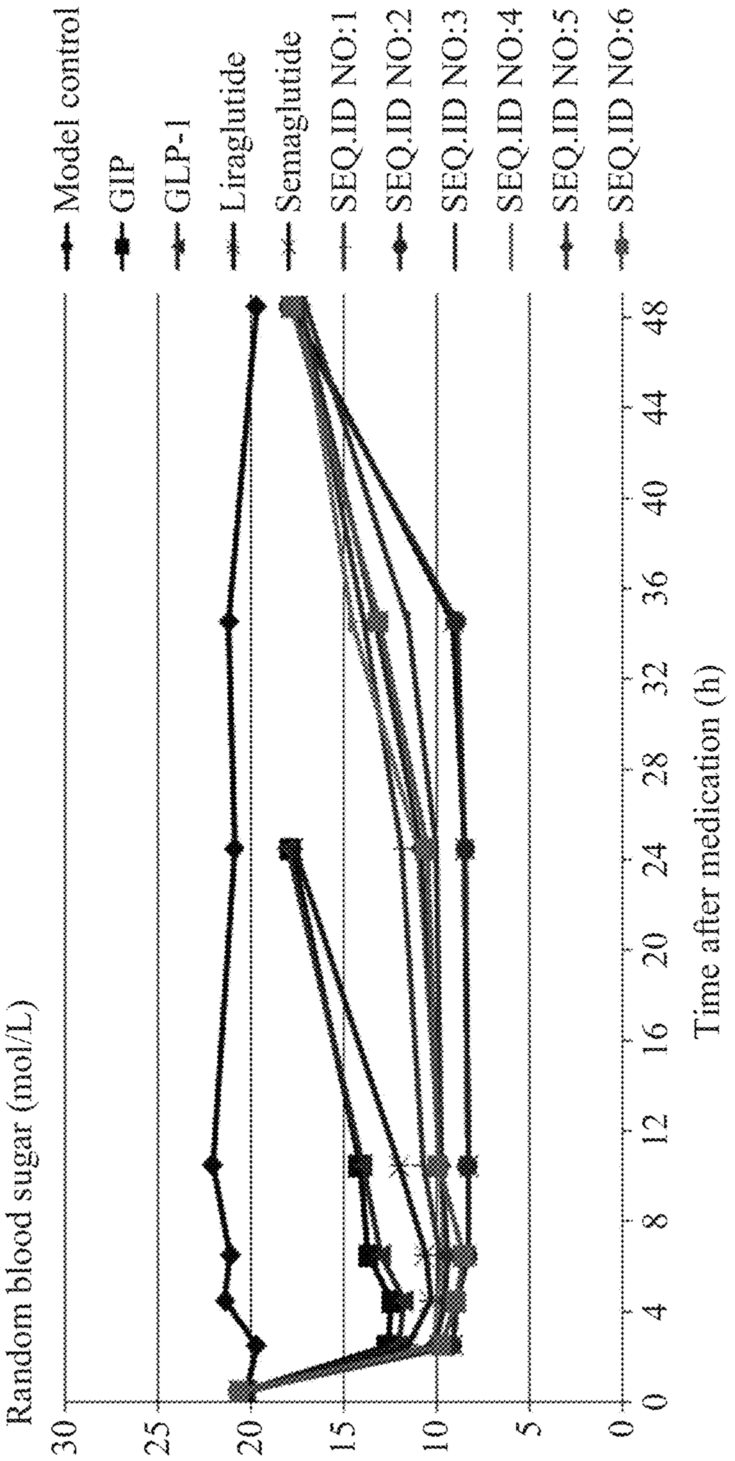
FIG. 1 and FIG. 2 are diagrams showing the effect of single administration of each test substance on random blood glucose and $AUC_{0\text{-}24h\ Glu}$ Glu in ob/ob mice (X±s, n=7)

The disclosure is described with the following embodiments, but these embodiments do not constitute any limitation to the rights of the disclosure.

Example 1

Synthesis of polypeptide compound of ID NO: 1:

YVEGTFTSDYSIVLDKIAQK(HOOC-$(CH_2)_{16}$-CO-γ-Glu-AEEA-AEEA)AFVQWLIAGGPSSGAPPPS-$NH_2$

1. Synthesis of Peptide Chain 1.1 Swelling of Resin 10 g of Fmoc-Rink Amide AM Resin (with the substitution degree of 0.35 mmol/g) was weighed and swelled for 30 min with 100 mL of DCM, suction filtration was conducted to remove DCM, swelling was conducted for 30 min with 100 mL of DMF, and the resin was washed with 100 mL of DMF and 100 mL of DCM respectively.

Synthesis of Fmoc-Ser(tBu)-Rink Amide AM Resin

Fmoc-Ser(tBu)-OH (8 mmol), HOBT (16 mmol) and DIC (16 mmol) were dissolved in 100 mL of DMF, then the solution was added into resin obtained in the previous step to react for 2 hours, after reaction ended, the reaction solution was filtered out, and the resin was washed 3 times with 100 mL of DCM and 100 mL of DMF respectively.

1.3 Removal of Fmoc Protecting Group

A 25% piperidine/DMF (V/V) solution containing 0.1 M of HoBt was added into the washed resin to remove Fmoc, and after the reaction ended, the resin was washed 3 times with 100 mL of DCM and 100 mL of DMF respectively.

1.4 Extension of Peptide Chain

According to the sequence, the steps of deprotection and coupling were repeated to sequentially bind corresponding amino acids, and the corresponding amino acids were sequentially bound until peptide chain synthesis was completed, to obtain the peptide resin.

The $20^{th}$ K could adopt a Fmoc-Lys(Alloc)-OH or Fmoc-Lys(Dde)-CH or Fmoc-Lys(iVdde)-OH or Fmoc-Lys(Mtt)-OH or Fmoc-Lys(Boc)-OH protection strategy. In this example, the Fmoc-Lys(Alloc)-OH protection strategy was adopted.

1.5 Splicing of Side Chains

The obtained peptide resin was put into a reaction bottle, and an Alloc protecting group was removed by using $Pd(PPH_3)_4$ under the condition that $PhSiH_3$ was used as a scavenger; and a 20-site Lys side chain was synthesized by adopting an Fmoc/t-Bu strategy, or Oct(OtBu)-γ-Glu(OtBu)-AEEA-AEEA-Osu fragments were directly coupled to obtain the fully-protected peptide resin.

1.6 Cleavage of Peptide Resin

Trifluoroacetic acid was measured to a reactor and cooled to −10° C. to 0° C., triisopropylsilane, 1,2-dithioglycol and purified water were added and stirred to be uniformly mixed. Peptide resin was slowly added, heated to 20-30° C., and a cracking reaction was conducted for 115-125 min. After the reaction ended, the resin was filtered out, the filtered resin was washed with M×8×20% ml of TFA, the filtered solution and the washing solution were completely transferred into M×8×1.2×4 ml of diethyl ether, stirred for 5-10 min, kept standing to precipitate for 15 min or more. The precipitated turbid liquid was added into a centrifugal machine, and solids were centrifuged and collected; the solids were washed with diethyl ether six times, and the amount of diethyl ether used each time was not less than 5 L. The solids were subjected to vacuum drying for 6-10 h t the temperature of 20-35° C., and crude peptide was obtained.

1.7 Purification of Crude Peptide

Purification was conducted through preparative liquid chromatography, and the chromatographic conditions were that a C18 column (100 mm×250 mm, 10 μm) was adopted; a mobile phase A was 0.1% TFA/water (V/V), and a mobile phase B was 0.1% TFA/acetonitrile (V/V); the mobile phase gradient was 20%-60% of the mobile phase B, and the time was 60 min; the flow velocity was 200 mL/min, the detection wavelength was 214 nm, fractions with the purity larger than 98.0% were collected, and 1.36 g of samples were obtained through freeze drying after rotary evaporation and concentration.

Example 2

Synthesis of polypeptide compound of ID NO: 2:

YXEGTFTSDYSIXLDKIAQK(HOOC-$(CH_2)_{16}$-CO-γ-Glu-AEEA-AEEA)AFVQWLIAGGPSSGAPPPS-$NH_2$

X= 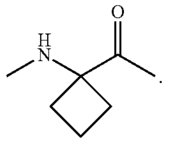

The synthesis procedures were the same as those in Example 1, and the collected solution was freeze-dried to obtain a purified product in a mass of 1.45 g.

Example 3

Synthesis of polypeptide compound of ID NO: 3:

YXEGTFTSDYSIXLDKIAQK(HOOC-$(CH_2)_{16}$-CO-γ-Glu-AEEA-AEEA)AFVQWLIAGGPSSGAPPPS-$NH_2$

X= 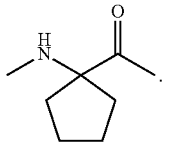

The synthesis procedures were the same as those in Example 1, and the collected solution was freeze-dried to obtain a purified product in a mass of 1.51 g.

Example 4

Synthesis of polypeptide compound of ID NO: 4:

YAEGTFTSDYSIALDKIAQK(HOOC-$(CH_2)_{16}$-CO-γ-Glu-AEEA-AEEA)AFVQWLIAGGPSSGAPPPS-$NH_2$

The synthesis procedures were the same as those in Example 1, and the collected solution was freeze-dried to obtain a purified product in a mass of 1.18 g.

Example 5

Synthesis of polypeptide compound of ID NO: 5:

YAEGTFTSDYSIAibLDKIAQK(HOOC-$(CH_2)_{16}$-CO-γ-Glu-AEEA-AEEA)AFVQWLIAGGPSSGAPPPS-$NH_2$

The synthesis procedures were the same as those in Example 1, and the collected solution was freeze-dried to obtain a purified product in a mass of 1.22 g.

Example 6

Synthesis of polypeptide compound of ID NO: 6:

YAibEGTFTSDYSIALDKIAQK(HOOC-$(CH_2)_{16}$-CO-γ-Glu-AEEA-AEEA)AFVQWLIAGGPSSGAPPPS-$NH_2$

The synthesis procedures were the same as those in Example 1, and the collected solution was freeze-dried to obtain a purified product in a mass of 1.97 g.

Example 7

Synthesis of polypeptide compound of ID NO: 7:

YX1EGTFTSDYSIX2LDKIAQK(HOOC-$(CH_2)_{16}$-CO-γ-Glu-AEEA-AEEA)AFVQWLIAGGPSSGAPPPS-$NH_2$ $X_1$= 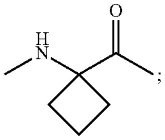

$X_2$=Aib.

The synthesis procedures were the same as those in Example 1, and the collected solution was freeze-dried to obtain a purified product in a mass of 1.55 g.

Example 8

Synthesis of polypeptide compound of ID NO: 8:

Y$X_1$EGTFTSDYSI$X_2$LDKIAQK(HOOC-$(CH_2)_{16}$-CO-γ-Glu-AEEA-AEEA)AFVQWLIAGGPSSGAPPPS-$NH_2$ $X_1$=Aib;

$X_2$= 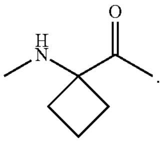 .

The synthesis procedures were the same as those in Example 1, and the collected solution was freeze-dried to obtain a purified product in a mass of 1.01 g.

Example 9

Synthesis of polypeptide compound of ID NO: 9:

$YX_1EGTFTSDYSIX_2LDKIAQK(HOOC-(CH_2)_{16}$-CO-γ-Glu-AEEA-AEEA)AFVQWLIAGGPSSGAPPPS-$NH_2$ $X_1$= 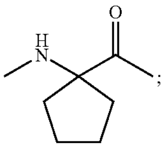 ;

$X_2$=Aib.

The synthesis procedures were the same as those in Example 1, and the collected solution was freeze-dried to obtain a purified product in a mass of 1.64 g.

Example 10

Synthesis of polypeptide compound of ID NO: 10:

$YX_1EGTFTSDYSIX_2LDKIAQK(HOOC-(CH_2)_{16}$-CO-γ-Glu-AEEA-AEEA)AFVQWLIAGGPSSGAPPPS-$NH_2$ $X_1$=Aib;

$X_2$= 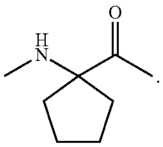 .

The synthesis procedures were the same as those in Example 1, and the collected solution was freeze-dried to obtain a purified product in a mass of 1.81 g.

Example 11

Synthesis of polypeptide compound of ID NO: 11:

YAibEGTFTSDYSIAibLDKIAQK(γ-Glu-Palmitoyl)AFVQWLIAG

GPSSGAPPPS-$NH_2$

The synthesis procedures were the same as those in Example 1, and the collected solution was freeze-dried to obtain a purified product in a mass of 1.84 g.

Example 12

Synthesis of polypeptide compound of ID NO: 12:

YVEGTFTSDYSIVLDKIAQK(γ-Glu-Palmitoyl)AFVQWLIAGGPS SGAPPPS-$NH_2$

The synthesis procedures were the same as those in Example 1, and the collected solution was freeze-dried to obtain a purified product in a mass of 1.12 g.

Example 13

Synthesis of polypeptide compound of ID NO: 13:

YXEGTFTSDYSIXLDKIAQK(γ-Glu-Palmitoyl)AFVQWLIAGGPS SGAPPPS-$NH_2$

X= 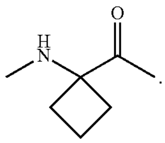 .

The synthesis procedures were the same as those in Example 1, and the collected solution was freeze-dried to obtain a purified product in a mass of 1.07 g.

Example 14

Synthesis of polypeptide compound of ID NO: 14:

YXEGTFTSDYSIXLDKIAQK(γ-Glu-Palmitoyl)AFVQWLIAGGPS SGAPPPS-$NH_2$

X= 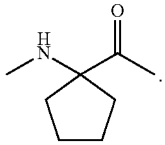 .

The synthesis procedures were the same as those in Example 1, and the collected solution was freeze-dried to obtain a purified product in a mass of 1.89 g.

Example 15

Synthesis of polypeptide compound of ID NO: 15:

YAEGTFTSDYSIALDKIAQK(γ-Glu-Palmitoyl)AFVQWLIAGGPS SGAPPPS-$NH_2$

The synthesis procedures were the same as those in Example 1, and the collected solution was freeze-dried to obtain a purified product in a mass of 1.81 g.

Example 16

Synthesis of polypeptide compound of ID NO: 16:

YAEGTFTSDYSIAibLDKIAQK(γ-Glu-Palmitoyl)AFVQWLIAGG PSSGAPPPS-$NH_2$

The synthesis procedures were the same as those in Example 1, and the collected solution was freeze-dried to obtain a purified product in a mass of 1.71 g.

Example 17

Synthesis of polypeptide compound of ID NO: 17:

YAibEGTFTSDYSIALDKIAQK(γ-Glu-Palmitoyl)AFVQWLIAGG PSSGAPPPS-$NH_2$

The synthesis procedures were the same as those in Example 1, and the collected solution was freeze-dried to obtain a purified product in a mass of 1.53 g.

Example 18

Synthesis of polypeptide compound of ID NO: 18:

YX1EGTFTSDYSIX2LDKIAQK(γ-Glu-Palmitoyl)AFVQWLIAGG PSSGAPPPS-$NH_2$ $X_1$= 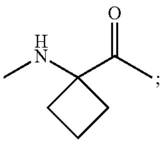 ;

$X_2$=Aib.

The synthesis procedures were the same as those in Example 1, and the collected solution was freeze-dried to obtain a purified product in a mass of 1.25 g.

Example 19

Synthesis of polypeptide compound of ID NO: 19:

YX$_1$EGTFTSDYSIX$_2$LDKIAOK(γ-Glu-Palmitoyl)AFVOWLIAGG PSSGAPPPS-$NH_2$ $X_1$=Aib;

$X_2$= 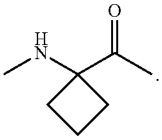 .

The synthesis procedures were the same as those in Example 1, and the collected solution was freeze-dried to obtain a purified product in a mass of 0.93 g.

Example 20

Synthesis of polypeptide compound of ID NO: 20:

YX$_1$EGTFTSDYSIX$_2$LDKIAQK(γ-Glu-Palmitoyl)AFVQWLIAGG PSSGAPPPS-$NH_2$ $X_1$= 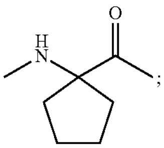 ;

$X_2$=Aib.

The synthesis procedures were the same as those in Example 1, and the collected solution was freeze-dried to obtain a purified product in a mass of 0.96 g.

Example 21

Synthesis of polypeptide compound of ID NO: 15:

YX$_1$EGTFTSDYSIX$_2$LDKIAQK(γ-Glu-Palmitoyl)AFVQWLIAGG PSSGAPPPS-$NH_2$ $X_1$=Aib;

$X_2$= 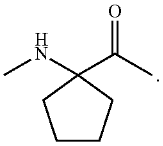 .

The synthesis procedures were the same as those in Example 1, and the collected solution was freeze-dried to obtain a purified product in a mass of 1.47 g.

Example 22

The relevant pharmacological experimental methods and results of a GIP and GLP-1 dual agonist polypeptide compound (hereinafter referred to as a polypeptide compound):

1. GLP-1 and GIP Rceptor Agonist Activity of Polypeptide Compound

HEK293 cells were co-transfected with cDNA encoding GLP-1R or GIPR. In a test for determining the compound, the cells were inoculated in a 96-well plate 2 h in advance, the polypeptide compound was dissolved with DMSO, and diluted to different multiples with a culture medium containing 0.1% bovine serum albumin and added to the co-transfected cells. After the cells were incubated for 20 min, fluorescence values were determined through microplate reader of an ELISA kit of the Cisbo Company, a standard curve was established to convert the fluorescence values into corresponding cAMP values, and the $EC_{50}$ value of the compound was calculated through nonlinear regression of Graphpad Prism 5.0 software.

TABLE 1

| Agonist activity of polypeptide compound on GLP-1R and GIPR | | | | | |
|---|---|---|---|---|---|
| Peptides | mGLP-1R $EC_{50}$ (nM) | mGIPR EC50 (nM) | Peptides | mGLP-1R EC50 (nM) | mGIPR EC50 (nM) |
| Semaglutide | 0.0076 | 68 | GIP | \ | 0.0011 |
| GLP-1 | 0.00127 | \ | ID NO: 11 | 0.02427 | 0.00632 |
| ID NO: 1 | 0.01457 | 0.00068 | ID NO: 12 | 0.05613 | 0.00879 |
| ID NO: 2 | 0.00613 | 0.00086 | ID NO: 13 | 0.05396 | 0.02250 |
| ID NO: 3 | 0.00396 | 0,00149 | ID NO: 14 | 0.03109 | 0.05165 |
| ID NO: 4 | 0.00149 | 0.00521 | ID NO: 15 | 0.04290 | 0.05320 |
| ID NO: 5 | 0.00299 | 0.00640 | ID NO: 16 | 0.04250 | 0.00965 |
| ID NO: 6 | 0.00258 | 0.00929 | ID NO: 17 | 0.04541 | 0.00972 |
| ID NO: 7 | 0.00549 | 0.00766 | ID NO: 18 | 0.00902 | 0.00833 |
| ID NO: 8 | 0.00805 | 0.00858 | ID NO: 19 | 0.01189 | 0.00791 |
| ID NO: 9 | 0.00941 | 0.00698 | ID NO: 20 | 0.01587 | 0.00591 |
| ID NO: 10 | 0.00889 | 0.00811 | ID NO: 21 | 0.01783 | 0.00807 |

As shown in Table 1, the agonist activity of all polypeptide compounds to GLP-1R still kept a high degree of agonist activity, and meanwhile kept a quite high degree of agonist activity to GIPR, and modified non-natural amino acids and side chain groups did not produce great influence on the agonist activity.

2. Blood Glucose Reducing Experiment of Polypeptide Compound

Male ob/ob mice were fed with high-fat feed in a single cage after weaning, blood glucose was predicted after 6-7 weeks, and the mice were divided into a model control group, a polypeptide compound group (selecting 9 compounds), a positive control Liraglutide group and a positive control Semaglutide group according to random weight, random blood glucose and fasting blood glucose. The mice in each test group and the positive control group received a single subcutaneous injection of test substances or positive drugs Liraglutide and Semaglutide at different doses, the mice in the model control group received a single subcutaneous injection of a PBS buffer solution. The mice in each group received random blood glucose value measurement before (0 h) administration and 2, 4, 6, 10 and 24 h after administration, and then the time for measuring the random blood glucose was adjusted and prolonged to 34, 48, 58 or 72 h after administration according to the blood glucose condition of the mice in each group. Meanwhile, the random weight of the mice in each group before (0 h) administration and 24 h after administration was weighed, and then the random weight of the mice corresponding to the random blood glucose measurement condition 48 or 72 h after administration was weighed. The blood glucose decrease rate, the blood glucose curve area ($AUC_{0\text{-}24h\ Glu}$) within 24 h after administration and the decrease rate were calculated according to the following formula.

Blood glucose decrease rate=(blood glucose in the model control group−blood glucose in the administration group)/blood glucose in the model control group×100%

$$AUC_{0-24h\,Glu}(mmol/Lh\cdot r) = (BG0+BG2)+(BG2+BG4)+(BG4+BG6)+(BG6+BG10)\times 2+(BG10+BG24)\times 7$$

BG0, BG2, BG4, BG6, BG10 and BG24 represented the blood glucose values before administration (0h) and 2, 4, 6, 10 and 24 h after administration respectively.

$AUC_{0\text{-}24h\ Glu}$(mmol/Lh·r) decrease rate=(model control group $AUC_{0\text{-}24h\ Glu}$−administration group $AUC_{0\text{-}24\ h\ Glu}$/model control group $AUC_{0\text{-}24h\ Glu}$×100%

Experiments were carried out twice, at an interval of 8-10 days. There were 23 groups in each experiment, and the experiment grouping and dosage setting conditions were shown in Table 2.

TABLE 2

| Grouping of experimental animals before administration (X ± s) | | | | |
|---|---|---|---|---|
| Groups | Dosage (μg/kg) | Random body weight (g) | Random blood glucose mmol/L) | Fasting blood glucose (mmol/L) |
| Model control | | 42.0 ± 300,8 | 20.23 ± 301.01 | 18.94 ± 300.99 |
| GLP | 100 | 42.5 ± 00.8 | 20.36 ± 300.74 | 18.97 ± 300.64 |
| GLP-1 | 100 | 42.3 ± 300.7 | 20.30 ± 301.05 | 19.34 ± 301.07 |
| Liraglutide | 100 | 42.1 ± 01.1 | 20.14 ± 300.98 | 18.86 ± 301.28 |
| Semiaglutide | 100 | 42.3 ± 01.0 | 20.71 ± 301.14 | 18.83 ± 300.85 |
| ID NO: 1 | 100 | 42.2 ± 300,5 | 20.31 ± 300.99 | 18.59 ± 300.68 |
| ID NO: 2 | 100 | 41.3 ± 300,8 | 20.62 ± 301.03 | 18.76 ± 300.75 |
| ID NO: 3 | 100 | 42.1 ± 300.5 | 20.45 ± 300.91 | 18.72 ± 301.02 |
| ID NO: 4 | 100 | 42.6 ± 301.0 | 20.43 ± 300,68 | 18.82 ± 300.75 |
| ID NO: 5 | 100 | 42.4 ± 300.9 | 20.57 ± 300.84 | 18.57 ± 301.14 |
| ID NO: 6 | 100 | 42.6 ± 300.6 | 20.64 ± 300.77 | 19.15 ± 300.80 |
| ID NO: 7 | 100 | 42.7 ± 01.0 | 20.64 ± 300.99 | 18.97 ± 300.69 |
| ID NO: 8 | 100 | 42.8 ± 300.7 | 20.36 ± 300.87 | 18.84 ± 300.78 |
| ID NO: 9 | 100 | 42.4 ± 00.8 | 20.24 ± 300.95 | 19.02 ± 300.73 |

Figure 2:
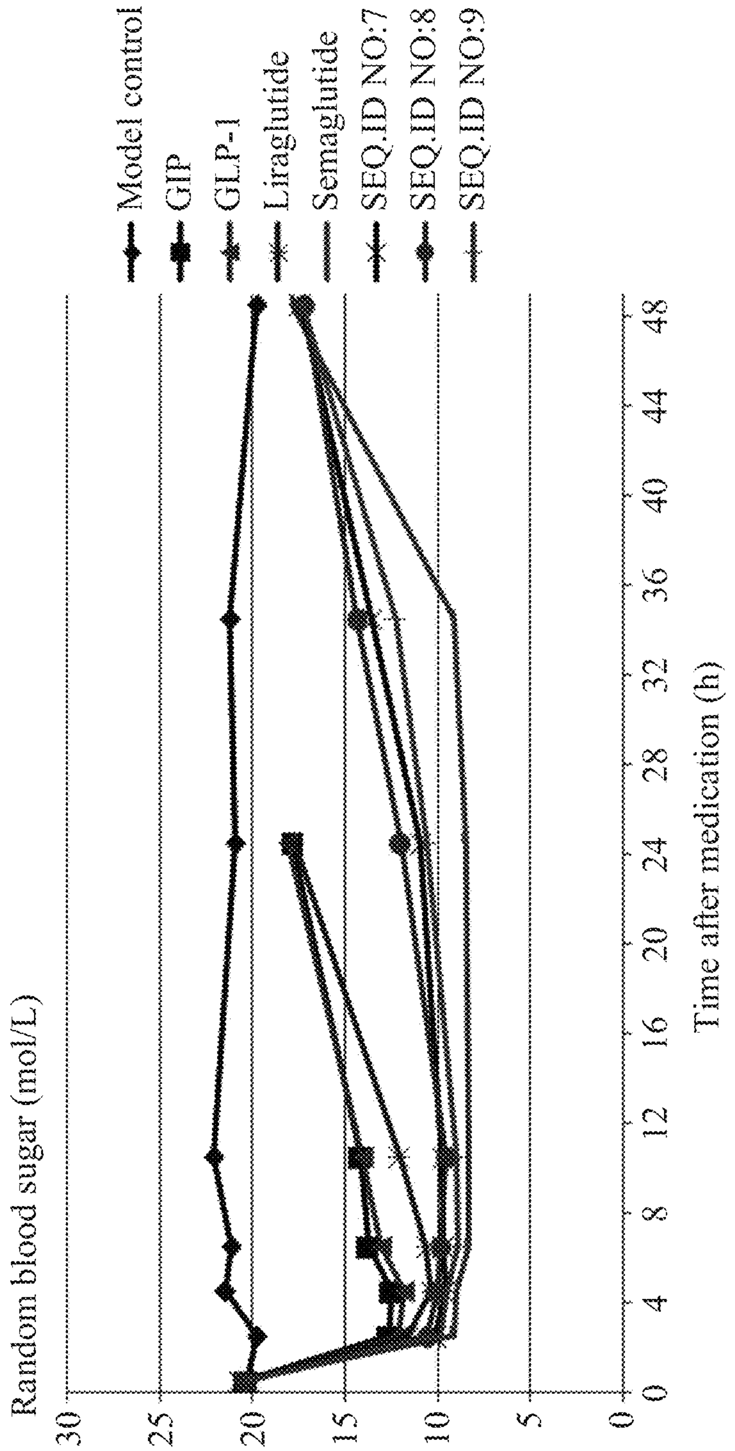
Figure 3:
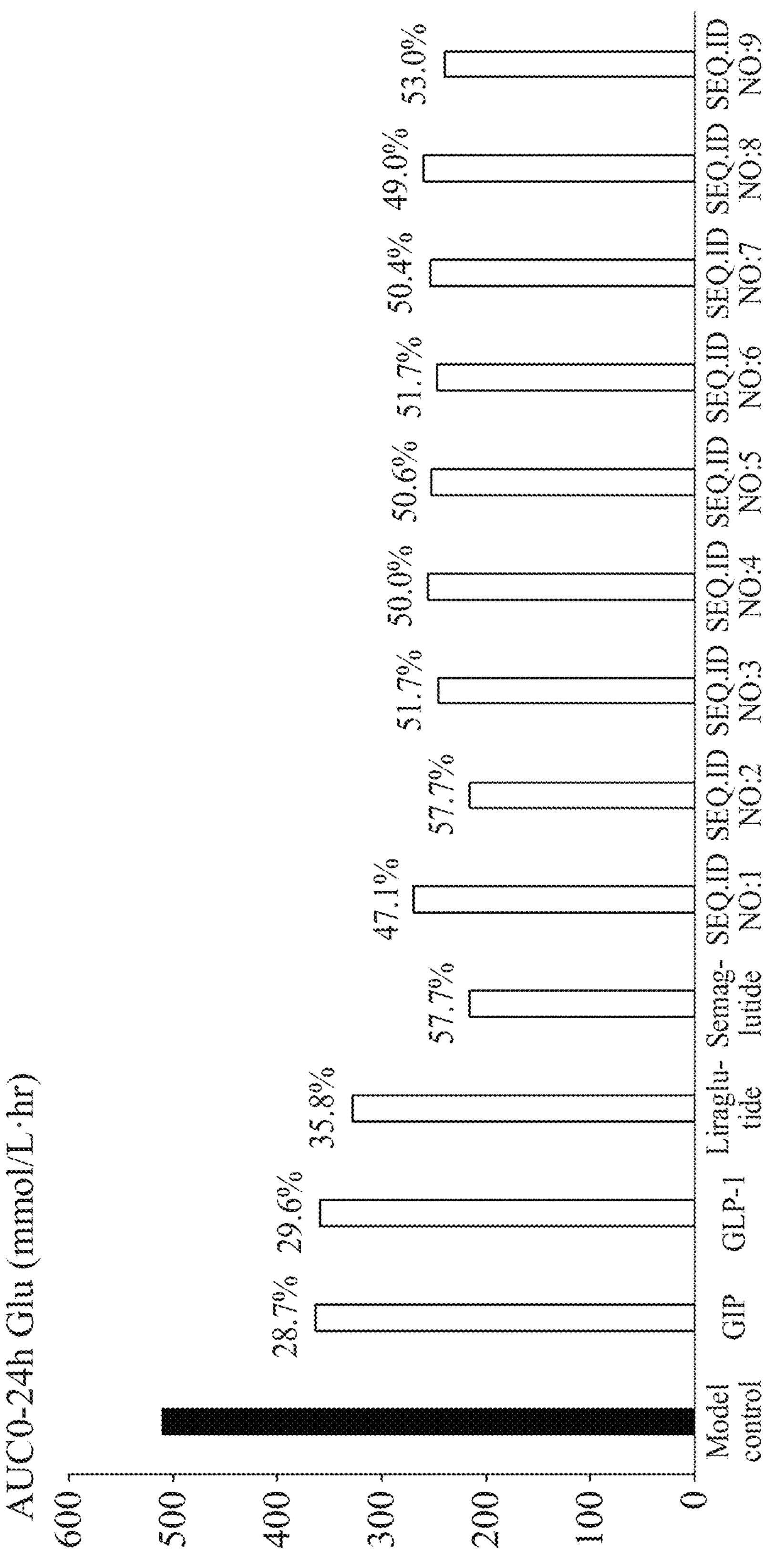
FIG. 3 is a diagram showing the effect of single administration of each test substance on AUC0-24h Glu in ob/ob mice (X±s, n=7) (data in the diagram is AUC0-24h Glu decrease rate).

As shown in FIG. 1 to FIG. 3, blood glucose reducing experiment results showed that, when the administration concentration of the polypeptide compound was 100 μg/kg, most of the blood glucose reducing effects were equivalent to those of Semaglutide and GIP, and especially the blood glucose reducing effect of ID NO: 2 was almost consistent with that of Semaglutide.

3. Effect of Polypeptide Compound on Random Weight of ob/ob Mmice

As shown in Tables 3 to 5, single subcutaneous injection administration of 100 g/kg of GIP and 100 g/kg of GLP-1 and 300 g/kg of GLP-1 had no obvious influence on the random weight and the variable quantity of the ob/ob mice. After a single subcutaneous injection administration of 100 g/kg of Liraglutide and Semaglutide groups, the random weight and the variable quantity of the ob/ob mice could be significantly reduced in 24 h and 48 h following the administration. After a single subcutaneous injection administration of 300 g/kg of ID NO: 1-9, the random weight and the variable quantity of the ob/ob mice could be significantly reduced in 24 h, 48 h and 72 h following the administration. After a single subcutaneous injection administration of 100 g/kg of ID NO: 2, the random weight variable quantity of the ob/ob mice could be significantly reduced in 24 hours following the administration. After a single subcutaneous injection administration of 300 g/kg of ID NO: 9, the random weight variable quantity of the ob/ob mice could be significantly reduced in 24 h and 48 h following the administration; and the effect of ID NO: 2 was basically equivalent to that of the equal dose of Semaglutide. Therefore, the single subcutaneous injection administration of the GIP and GLP-1 dual agonist compound could significantly reduce the random blood glucose of the type 2 diabetes ob/ob mice, wherein the effect of ID NO: 2 was comparable to that of the equal dose of Semaglutide. After long-term administration, all polypeptide compounds showed a better weight control effect.

TABLE 3

Effect of single administration of each test substance on random blood glucose and $AUC_{0\text{-}24\ h\ Glu}$ in ob/ob mice ($\overline{X}$ ± s, n = 7)

| Groups | Dosage (μg/kg) | Blood glucose at different time after administration (mmol/L) 0 h | 2 h | 4 h | 6 h | 10 h | 24 h | 34 h | 48 h | $AUC_{0\text{-}24\ h\ Glu}$ (mmol/L hr) |
|---|---|---|---|---|---|---|---|---|---|---|
| Model control | — | 20.23 ± 1.01 | 19.72 ± 1.86 | 21.43 ± 1.92 | 21.12 ± 1.07 | 22.06 ± 1.83 | 20.89 ± 1.08 | 21.19 ± 1.14 | 19.71 ± 2.31 | 510.66 ± 24.79 |
| GIP | 100 | 20.36 ± 0.74 | 12.63 ± 1.70 | 12.46 ± 1.66 | 13.71 ± 0.86 | 14.16 ± 1.24 | 17.84 ± 0.87 | — | — | 363.99 ± 14.21 |
| GLP-1 | 100 | 20.30 ± 1.05 | 12.06 ± 1.36 | 11.79 ± 0.84 | 13.02 ± 0.86 | 14.03 ± 2.41 | 18.04 ± 0.71 | — | — | 359.61 ± 18.59 |
| Liraglutide | 100 | 20.14 ± 0.98 | 11.56 ± 1.12 | 10.34 ± 1.30 | 10.63 ± 0.84 | 12.03 ± 0.81 | 17.71 ± 1.08 | — | — | 328.07 ± 19.12 |
| Semaglutide | 100 | 20.71 ± 1.14 | 9.12 ± 0.84 | 8.96 ± 1.40 | 8.32 ± 0.88 | 8.29 ± 0.86 | 8.49 ± 1.12 | 9.12 ± 0.83 | 17.83 ± 1.42 | 215.87 ± 18.67 |
| ID NO: 1 | 100 | 20.31 ± 0.99 | 10.12 ± 0.87 | 9.94 ± 0.86 | 9.83 ± 0.87 | 10.76 ± 1.12 | 11.89 ± 2.12 | 13.93 ± 1.01 | 17.32 ± 0.89 | 269.99 ± 19.45 |
| ID NO: 2 | 100 | 20.62 ± 1.03 | 9.14 ± 0.83 | 8.95 ± 0.84 | 8.33 ± 1.42 | 8.31 ± 1.02 | 8.51 ± 0.86 | 8.95 ± 0.87 | 18.01 ± 1.12 | 216.15 ± 18.86 |
| ID NO: 3 | 100 | 20.45 ± 0.91 | 10.11 ± 1.01 | 9.52 ± 1.02 | 9.63 ± 2.42 | 9.76 ± 1.13 | 10.01 ± 1.42 | 11.56 ± 0.97 | 17.06 ± 1.21 | 246.51 ± 24.91 |
| ID NO: 4 | 100 | 20.43 ± 0.68 | 10.21 ± 1.06 | 9.89 ± 0.83 | 9.63 ± 0.95 | 9.86 ± 0.96 | 11.01 ± 0.83 | 14.56 ± 1.42 | 17.32 ± 0.83 | 255.33 ± 20.13 |
| ID NO: 5 | 100 | 20.57 ± 0.84 | 10.12 ± 1.20 | 9.54 ± 0.84 | 9.43 ± 0.86 | 9.76 ± 0.96 | 10.89 ± 1.43 | 13.33 ± 2.10 | 17.32 ± 1.12 | 252.25 ± 19.68 |
| ID NO: 6 | 100 | 20.64 ± 0.77 | 9.76 ± 0.83 | 8.96 ± 0.77 | 8.55 ± 0.96 | 9.93 ± 0.76 | 10.53 ± 1.21 | 13.13 ± 2.21 | 17.79 ± 0.86 | 246.81 ± 18.95 |
| ID NO: 7 | 100 | 20.64 ± 0.99 | 10.11 ± 0.88 | 9.58 ± 0.97 | 9.66 ± 0.84 | 9.76 ± 0.79 | 10.93 ± 0.86 | 13.54 ± 1.24 | 17.34 ± 1.20 | 253.35 ± 18.65 |
| ID NO: 8 | 100 | 20.36 ± 0.87 | 10.56 ± 0.99 | 9.99 ± 0.86 | 9.83 ± 0.85 | 9.54 ± 1.12 | 11.95 ± 1.26 | 14.33 ± 1.43 | 17.16 ± 1.52 | 260.46 ± 21.31 |
| ID NO: 9 | 100 | 20.24 ± 0.95 | 9.85 ± 0.89 | 9.51 ± 0.97 | 8.92 ± 0.86 | 8.93 ± 0.86 | 10.57 ± 0.83 | 12.26 ± 0.94 | 17.28 ± 1.28 | 240.08 ± 18.97 |

TABLE 4

Decrease rate of random blood glucose and $AUC_{0\text{-}24\ h\ Glu}$ in ob/ob mice after single administration of each test substance ($\overline{X}$ ± s, n = 7)

| Groups | Dosage (μg/kg) | Decrease rate of blood glucose at different time after administration (%) 2 h | 4 h | 6 h | 10 h | 24 h | 34 h | 48 h | $AUC_{0\text{-}24\ h\ Glu}$ Decrease rate (%) |
|---|---|---|---|---|---|---|---|---|---|
| GIP | 100 | 38.0 | 38.8 | 32.7 | 30.5 | 12.4 | — | — | 28.7 |
| GLP-1 | 100 | 40.6 | 41.9 | 35.9 | 30.9 | 11.1 | — | — | 29.6 |
| Liraglutide | 100 | 42.6 | 48.7 | 47.2 | 40.3 | 12.1 | — | — | 35.8 |
| Semaglutide | 100 | 56.0 | 56.7 | 59.8 | 60.0 | 59.0 | 56.0 | 13.9 | 57.7 |
| ID NO: 1 | 100 | 50.2 | 51.1 | 51.6 | 47.0 | 41.5 | 31.4 | 14.7 | 47.1 |
| ID NO: 2 | 100 | 55.7 | 56.6 | 59.6 | 59.7 | 58.7 | 56.6 | 12.7 | 57.7 |
| ID NO: 3 | 100 | 50.6 | 53.4 | 52.9 | 52.3 | 51.1 | 43.5 | 16.6 | 51.7 |
| ID NO: 4 | 100 | 50.0 | 51.6 | 52.9 | 51.7 | 46.1 | 28.7 | 15.2 | 50.0 |
| ID NO: 5 | 100 | 50.8 | 53.6 | 54.2 | 52.6 | 47.1 | 35.2 | 15.8 | 50.6 |
| ID NO: 6 | 100 | 52.7 | 56.6 | 58.6 | 51.9 | 49.0 | 36.4 | 13.8 | 51.7 |
| ID NO: 7 | 100 | 51.0 | 53.6 | 53.2 | 52.7 | 47.0 | 34.4 | 16.0 | 50.4 |

TABLE 4-continued

Decrease rate of random blood glucose and $AUC_{0-24\ h\ Glu}$ in ob/ob mice after single administration of each test substance ($\overline{X}$ ± s, n = 7)

| Groups | Dosage (μg/kg) | Decrease rate of blood glucose at different time after administration (%) 2 h | 4 h | 6 h | 10 h | 24 h | 34 h | 48 h | $AUC_{0-24\ h\ Glu}$ Decrease rate (%) |
|---|---|---|---|---|---|---|---|---|---|
| ID NO: 8 | 100 | 48.1 | 50.9 | 51.7 | 53.1 | 41.3 | 29.6 | 15.7 | 49.0 |
| ID NO: 9 | 100 | 51.3 | 53.0 | 55.9 | 55.9 | 47.8 | 39.4 | 14.6 | 53.0 |

TABLE 5

Effect of single administration of each test substance on random body weight and variable quantity in ob/ob mice ($\overline{X}$ ± s, n = 7)

| Groups | Dosage(μg/kg) | Random body weight at different time after administration (g) 0 h | 24 h | 48 h | Changes of random body weight at different time after administration (g) 0 h | 24 h | 48 h |
|---|---|---|---|---|---|---|---|
| Model control | — | 42.9 ± 0.8 | 43.5 ± 0.8 | 43.6 ± 0.7 | 0.0 ± 0.0 | 0.6 ± 0.1 | 0.7 ± 0.1 |
| GIP | 100 | 43.5 ± 0.8 | 43.6 ± 0.8 | — | 0.0 ± 0.0 | 0.1 ± 0.1 | — |
| GLP-1 | 100 | 43.2 ± 0.7 | 43.1 ± 0.7 | — | 0.0 ± 0.0 | −0.1 ± 0.1 | — |
| Liraglutide | 100 | 43.0 ± 1.1 | 42.6 ± 1.1 | — | 0.0 ± 0.0 | −0.5 ± 0.1 | — |
| Semaglutide | 100 | 43.7 ± 1.0 | 40.7 ± 1.0 | 41.7 ± 1.0 | 0.0 ± 0.0 | −2.9 ± 0.2 | −1.9 ± 0.2 |
| ID NO: 1 | 100 | 43.2 ± 0.5 | 42.0 ± 0.5 | 42.7 ± 0.6 | 0.0 ± 0.0 | −1.1 ± 0.2 | −0.6 ± 0.1 |
| ID NO: 2 | 100 | 43.3 ± 0.8 | 40.3 ± 0.8 | 41.3 ± 0.8 | 0.0 ± 0.0 | −2.9 ± 0.2 | −1.9 ± 0.2 |
| ID NO: 3 | 100 | 43.2 ± 0.5 | 41.6 ± 0.6 | 42.1 ± 0.6 | 0.0 ± 0.0 | −1.5 ± 0.2 | −0.9 ± 0.2 |
| ID NO: 4 | 100 | 43.6 ± 1.0 | 42.2 ± 1.0 | 42.9 ± 1.1 | 0.0 ± 0.0 | −1.4 ± 0.2 | −0.6 ± 0.1 |
| ID NO: 5 | 100 | 43.5 ± 0.9 | 42.0 ± 0.9 | 42.9 ± 0.9 | 0.0 ± 0.0 | −1.4 ± 0.2 | −0.6 ± 0.2 |
| ID NO: 6 | 100 | 43.5 ± 0.6 | 42.1 ± 0.7 | 42.7 ± 0.7 | 0.0 ± 0.0 | −1.5 ± 0.2 | −0.8 ± 0.1 |
| ID NO: 7 | 100 | 43.7 ± 1.0 | 42.1 ± 1.0 | 43.0 ± 0.9 | 0.0 ± 0.0 | −1.5 ± 0.2 | −0.7 ± 0.1 |
| ID NO: 8 | 100 | 43.8 ± 0.7 | 42.7 ± 0.7 | 43.2 ± 0.7 | 0.0 ± 0.0 | −1.1 ± 0.2 | −0.6 ± 0.1 |
| ID NO: 9 | 100 | 43.5 ± 0.8 | 41.5 ± 0.8 | 42.4 ± 0.9 | 0.0 ± 0.0 | −1.9 ± 0.2 | −1.1 ± 0.1 |

What is claimed is:

1. A GIP and GLP-1 dual agonist polypeptide compound, having an amino acid sequence as follows:

$YXaa^1EGTFSDYSIXaa^2LDKIAQXaa^3AFVQWLIAG$ GPSSGAPPPS (SEQ ID NO: 1), and a C-terminal amino acid of the polypeptide compound being amidated as a C-terminal primary amide; wherein:

$Xaa^1$ and $Xaa^2$ are

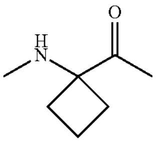
;

and $Xaa^3$ is:

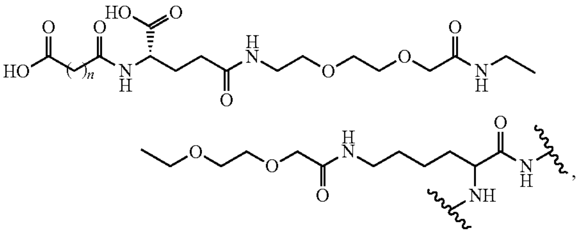
, and n is an integer number ranging from 5 to 25.

* * * * *

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Fully synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 1

Tyr Xaa Glu Gly Thr Phe Thr Ser Asp Tyr Ser Ile Xaa Leu Asp Lys
1               5                   10                  15

Ile Ala Gln Xaa Ala Phe Val Gln Trp Leu Ile Ala Gly Gly Pro Ser
            20                  25                  30
```

-continued

```
Ser Gly Ala Pro Pro Pro Ser
        35
```